(12) United States Patent
Fernández Tiburcio et al.

(10) Patent No.: US 9,139,841 B2
(45) Date of Patent: Sep. 22, 2015

(54) PLANT HAVING RESISTANCE TO LOW-TEMPERATURE STRESS AND METHOD OF PRODUCTION THEREOF

(75) Inventors: Antonio Fernández Tiburcio, Barcelona (ES); Teresa Altabella Artigas, Castelldefels (ES); Alejandro Ferrando Monleón, La Cañada-Paterna (ES)

(73) Assignees: UNIVERSIDAD DE BARCELONA, Barcelona (ES); UNIVERSITAT DE VALENCIA, Valencia (ES)

(*) Notice: Subject to any disclaimer, the term of this patent is extended or adjusted under 35 U.S.C. 154(b) by 239 days.

(21) Appl. No.: 13/003,735

(22) PCT Filed: Jul. 10, 2009

(86) PCT No.: PCT/ES2009/000363
§ 371 (c)(1),
(2), (4) Date: Jan. 13, 2011

(87) PCT Pub. No.: WO2010/004070
PCT Pub. Date: Jan. 14, 2010

(65) Prior Publication Data
US 2011/0126322 A1  May 26, 2011

(30) Foreign Application Priority Data
Jul. 11, 2008  (ES) .................................. 200802145

(51) Int. Cl.
*C12N 15/82* (2006.01)
*A01H 5/00* (2006.01)
*C12N 9/88* (2006.01)

(52) U.S. Cl.
CPC .............. *C12N 15/8273* (2013.01); *C12N 9/88* (2013.01)

(58) Field of Classification Search
USPC ........................................................ 800/289
See application file for complete search history.

(56) References Cited

U.S. PATENT DOCUMENTS
7,109,033 B2 * 9/2006 Harper et al. ................. 435/419

FOREIGN PATENT DOCUMENTS
WO   WO01/09358 A1   2/2001
WO   WO01/11062 A2   2/2001

OTHER PUBLICATIONS

Friedberg, Automated protein function prediction—the genomic challenge, 7 Briefings in Bioinformatics, 225-242 (2006).*
Han et al., Improvement in the Reproducibility and Accuracy of DNA Microarray Quanitification by Optimizing Hybridization Conditions, 7 BMC Bioinformatics Suppl 2 (2006).*
Young et al. (Putrescine and Acid Stress, 71 Plant Physiol., 767-771 at 767 (1983)).*
Masgrau et al., Inducible overexpression of oat arginine decarboxylase in transgenic tobacco plants, 11 Plant Journal, 465-473 (1997).*
Alcazar et al., Overexpression of ADC2 *Arabidopsis* induces dwarfism and late-flowering through GA deficiency, 43 Plant Journal, 425-436 (2005).*
Galloway et al., Phylogenetic Utility of the Nuclear Gene Arginine Decarboxylase: An Example from Brassicaceae, 15 Mol. Biol. Evol. No. 10, 1312-1320 at 1312 (1998); of record IDS Mar. 16, 2011).*
Capell et al. (Over-expression of the oat arginine decarboxylase cDNA in transgenic rice (*Oryza sativa* L.) affects normal development patterns in vitro and results in putrescine accumulation in transgenic plants, 97 Theor Appl Genet, 246-254 (1998)).*
Burtin et al., Overexpression of arginine decarboxylase in transgenic plants, 325 Biochem J, 331-337 at 335 (1997)).*
Watson et al. (Regulation of *Arabidopsis thaliana* (L.) Heynh Arginine Decarboxylase by Potassium Deficiency Stress, 111 Plant Physiol., 1077-1083 (1996)).*
GenBank Accession No. U52851 ; available at http://www.ncbi.nlm.nih.gov/nuccore/1590813, published Mar. 27, 1996.*
GenBank Accession No. AAB09723; available at http://www.ncbi.nlm.nih.gov/protein/1590814, published Mar. 27, 1996.*
Hummel et al., Characterization of the two arginine decarboxylase (polyamine biosynthesis) paralogues of the endemic subantarctic cruciferous species *Pringlea antiscorbutica* and analysis of their differential expression during development and response to environmental stress, 342 Gene, 199-209 at 203 (2004); of record IDS Mar. 16, 2011).*
Cook et al. (A prominent role for the CBF cold response pathway in configuring the low-temperature metabolome of *Arabidopsis*, 101 PNAS No. 42, 15243-15248 (2004)).*
Nemeth et al. (Exogenous salicyclic acid increases polyamine content but may decrease drought tolerance in maize, 162 Plant Science, 569-574 (2002)).*
PCT Application No. PCT/ES2009/000363 English Translation of the Written Opinion of the International Searching Authority dated Nov. 24, 2009.
PCT Application No. PCT/ES2009/000363 English Translation of the International Preliminary Report on Patentability issued by the International Bureau of WIPO dated Feb. 8, 2011.
Hummel, I., et al., "Differential gene espression of Arginine Decarboxylase ADCI and ADC2 in *Arabidopsis thaliana:* characterization of transcriptional regulation during seed germination and seedling development," New Phytologist; vol. 163, No. 3; Sep. 2004; pp. 519-531.
Alcázar, R., et al., "Overexpression of ADC2 in *Arabidopsis* induces dwarfism and late-flowering through GA dediciency," The Plant Journal; vol. 43, No. 3; Aug. 2005; pp. 425-436.

(Continued)

*Primary Examiner* — Cynthia Collins
*Assistant Examiner* — Russell Boggs
(74) *Attorney, Agent, or Firm* — Peter B. Scull; Hamilton, DeSanctis & Cha LLP

(57) ABSTRACT

The present invention relates to a method of production of plants having improved resistance to low-temperature stress, comprising a stage of conversion of the cells of a plant with a sequence of exogenous arginine decarboxylase gene ADC1 under control of a promoter capable of functioning in the plant. Plants thus obtained show resistance to low-temperature stress without the phenotype being affected when compared with the phenotype of plants of the wild type.

16 Claims, 6 Drawing Sheets

(56) References Cited

OTHER PUBLICATIONS

Hummel, I., et al., "Characterization of the two arginine decarboxylase (polyamine biosynthesis) paralogues of the endemic subantarctic cruciferous species *Pringlea antiscorbutica* and analysis of their differential expression during development and response to environmental stress," Gene; vol. 342, No. 2; Nov. 2004; pp. 199-209.

Galoway, et al., "Phylogenetic utility of the nuclear gene Arginine Decarboxylase: an example from Brassicaceae", Molecular Biology and Evolution; 1998; vol. 15; pp. 1312-1320.

Clough S. J., et al., "Floral dip: a simplified method for Agrobacterium-mediated transformation of *Arabidopsis thaliana*", The Plant Journal, 1998; vol. 16; pp. 735-743.

Murashige T. et al., "A revised medium for rapid growth and bioassays with tobacco tissue culture", Physiologia Plantarum; 1962; vol. 15; pp. 473-497.

Peirson S. N. et "Experimental validation of novel and conventional approaches to quantitative real-time PCR data analysis", Nucleic Acids Research; Oxford University Press 2003, vol. 31, No. 14, e73; 7 pages.

Tichopad A. et al., "Standardized determination of real-time PCR efficiency from a single reaction set-up", Nucleic Acids Research; Oxford University Press 2003; vol. 31, No. 20, e122; 6 pages.

Marcé M. et al., "Rapid high-perfomance liquid chromatographic method for quantitation of polyamines as their dansyl derivatives: Application to plant and animal tissues", Journal of Chromatography Biomedical Applications; 1995; vol. 666; pp. 329-335.

Horsch et al., "A simple and general method for transferring genes into plants", Science; 1985; vol. 227; pp. 1229-1231.

Altabella et al., "Putrescine as signaling molecule involved in the control of stress responses to cold and drought. Plant Abiotic Stress-from signaling to development", 2nd Meeting of the INPAS May 2009; Abstract; p. 32.

European Molecular Biology Laboratory—European Bioinformatics Institute (EMBL-EBI), BLAST alignment, ClustalW2 results, Clustal 2.1 multiple sequence alignment, dated May 31, 2012, http://www.ebi.ac.uk/tools/services/web/toolresult.ebi?jobId=clustalw . . . , Cambridgeshire, United Kingdom.

Hua Mo, et al., Up-regulation of arginine decarboxylase gene expression and accumulation of polyamines in mustard (*Brassica juncea*) in response to stress, Physiologia Plantarum 114, 2002 (the year of publication is sufficiently earlier than the effective U.S. filing date and any foreign priority date so that the particular month of publication is not in issue), pp. 439-449, Wiley-Blackwell for the Scandinavian Plant Physiology Society, Copenhagen,Denmark.

Caries Masgrau, et al., Inducible overexpression of oat arginine decarboxylase in transgenic tobacco plants, The Plant Journal, 1997 (the year of publication is sufficiently earlier than the effective U.S. filing date and any foreign priority date so that the particular month of publication is not in issue), pp. 465-473, 11, 3, Blackwell Publishing Ltd., headquarters Hoboken, New Jersey, in association with the Society for Experimental Biology, London, England.

Irene Hummel, et al., Characterization of the two arginine decarboxylase (polyamine biosynthesis) paralogues of the endemic subantartic cruciferous species *Pringlea antiscorbutica* and analysis of their differential expression during development and response to environmental stress, GENE, available online at www.sciencedirect.com on Oct. 12, 2004, pp. 199-209, GENE 342 (2004), Elsevier, Amsterdam, NL.

Daphne Preuss, Cultivation of *Arabidopsis*, Cold Spring Harbor Protocols, information at http://cshprotocols.cshlp.org/content/2006/5/pdb.ip22.short, published May 2006; accessed Dec. 5, 2013 (date accessed and downloaded), Cold Spring Harbor, NY, USA.

Celine Masclaux, et al., Characterization of the sink/source transition in tobacco (*Nicotiana tabacum* L.) shoots in relation to nitrogen management and leaf senescence, 2000 (the year of publication is sufficiently earlier than the effective U.S. filing date and any foreign priority date so that the particular month of publication is not in issue), vol. 211, pp. 510-518, Planta, Springer-Verlag, Germany.

Bruce Alberts, et al., Chapter 3, Proteins, Molecular Biology of the Cell, Fifth Edition, 2008, 2002, (the year of publication is sufficiently earlier than the effective U.S. filing date and any foreign priority date so that the particular month of publication is not in issue), pp. 125-126, 135-139, 155-156, Fifth Edition, Garland Science, Taylor & Francis Group, LLC, New York, NY USA.

Clustal Omega, Multiple Sequence Alignment Tool; The European Bioinformatics Institute Part of the European Molecular Biology Laboratory (aka EMBL-EBI) at http://www.ebi.ac.uki; Multiple Sequence Alignment Tool available at http://www.ebi.ac.uk/Tools/msa/clustalo/; Results attached here found at http://www.ebi.ac.uk/Tools/services/web/tooresult.ebi?jobId=clustalo-I20131204-080722-0366-845 . . . ; Results here generated on Dec. 4, 2013; EMBL-EBI, Wellcome Trust Genome Campus, Hinxton, Cambridgeshire, CB10 1SD, UK.

\* cited by examiner

A)

B)

ADC1: 804pb

Actin: 200pb

SEQUENCE LISTING

```
<160> NUMBER OF SEQ ID NOS: 16

<210> SEQ ID NO 1
<211> LENGTH: 2109
<212> TYPE: DNA
<213> ORGANISM: Arabidopsis thaliana

<400> SEQUENCE: 1
atgcctgctc tagcttttgt tgatactccc atcgatacct tttccagtat ctttacaccg      60
tcgtctgttt ccaccgccgt tgttgacggt tcctgccatt ggtctccgtc cctctcctcc     120
tctctttacc gtatcgacgg atggggagct ccgtatttcg cagcgaattc ctccgggaac     180
atctctgttc gtcctcatgg ctcaaacact ttacctcacc aagacatcga tctgatgaaa     240
gttgtgaaga aagttacaga tccgagtggt ttaggattac agcttccgct tattgttcgt     300
ttccctgatg ttctgaagaa tcgtcttgag tgtcttcaat ccgcgtttga ttacgcgatt     360
cagagtcaag gatatgattc tcattaccaa ggtgtgtatc ctgtgaaatg taatcaagat     420
cggtttatca tcgaagatat tgtcgaattc ggatccggtt ttcgattcgg tttagaagct     480
ggttccaagc ctgagattct tcttgctatg agttgtttgt gtaaaggtaa tcctgaagct     540
tttcttgtgt gtaatggttt taaagactct gagtatatct cattggcttt gtttgggagg     600
aaacttgaat tgaatactgt tattgttctt gagcaagaag aagagcttga tttggttatt     660
gatttgagcc agaagatgaa tgttaggcct gttattgggt taagagctaa gcttagaact     720
aaacattctg gtcattttgg ttctacttct ggtgagaagg ggaagtttgg tttgactacg     780
gttcagattc ttcgtgtggt gaggaagctg agtcaagttg gtatgcttga ttgtctccag     840
cttctgcatt tcacattgg ttcacagatt ccgtccacgg ctttgctttc cgacggtgtg     900
gctgaggctg cgcagcttta ctgtgagctt gtccgtcttg gtgctcatat gaaggtgatt     960
gatattggtg gtgggtggg gattgattac gacgggtcta atcggggga gtcggatctc    1020 tctgttgctt atagtctcga ggagtatgct gcagctgttg tggcttcggt taggtttgtt    1080
tgtgatcaga gtctgtgaa gcatccggtg atttgcagcg agagcggtcg agccattgtg    1140
tctcatcact cggtgttgat ctttgaagct gtctcagctg gtcaacaaca tgagacccct    1200
actgatcatc agtttatgct tgaagggtac tctgaggaag ttcgaggtga ttacgagaat    1260
ctttatggtg ctgctatgcg tggtgatcgt gaaagctgct tgctttatgt tgatcagctg    1320
aagcagagat gtgttgaagg gttcaaagaa ggttccttgg gcattgaaca gttagctggt    1380
gttgatggat tatgcgagtg ggtgattaag gcgattggtg catcggatcc ggttcttact    1440
taccatgtca atctatcggt tttcacttcg attcctgatt tctgggggat tgatcagctg    1500
tttcctattg ttccaatcca taaacttgac caaaggcctg ccgcgagagg gatcttatcg    1560
gatttgacgt gtgacagcga cggaaagatc aacaagttca taggcggaga atcgagcttg    1620
ccattgcacg agatggacaa caatggctgc agcggtgggc ggtactattt gggaatgttc    1680
ctaggtggag cttatgagga agctctcggt ggagtccaca atctgttcgg tggaccaagc    1740
```

-continued

```
gtggttcgcg tattgcagag cgatggacct cacggattcg cagtgacccg tgctgtgatg    1800
ggccaatcct ctgcagatgt cctcagagca atgcagcatg agcctgagct catgtttcag    1860
actcttaaac accgagccga ggagccgagg aacaacaaca acaaagcttg tggtgataag    1920
gggaacgaca aactagtagt cgcatcgtgt cttgctaagt cattcaacaa catgccttat    1980
ctttccatgg aaacgtcaac aaacgctctc accgcagcgg tcaataacct tggcgtttac    2040
tactgcgatg aagctgcagc tggtggcggc ggcaagggca agatgagaa ttggtcttat    2100 ttcggttga                                                           2109
```

<210> SEQ ID NO 2
<211> LENGTH: 702
<212> TYPE: PRT
<213> ORGANISM: Arabidopsis thaliana

<400> SEQUENCE: 2

```
Met Pro Ala Leu Ala Phe Val Asp Thr Pro Ile Asp Thr Phe Ser Ser
 1               5                  10                  15

Ile Phe Thr Pro Ser Ser Val Ser Thr Ala Val Val Asp Gly Ser Cys
            20                  25                  30

His Trp Ser Pro Ser Leu Ser Ser Leu Tyr Arg Ile Asp Gly Trp
        35                  40                  45

Gly Ala Pro Tyr Phe Ala Ala Asn Ser Ser Gly Asn Ile Ser Val Arg
    50                  55                  60

Pro His Gly Ser Asn Thr Leu Pro His Gln Asp Ile Asp Leu Met Lys
65                  70                  75                  80

Val Val Lys Lys Val Thr Asp Pro Ser Gly Leu Gly Leu Gln Leu Pro
                85                  90                  95

Leu Ile Val Arg Phe Pro Asp Val Leu Lys Asn Arg Leu Glu Cys Leu
            100                 105                 110

Gln Ser Ala Phe Asp Tyr Ala Ile Gln Ser Gln Gly Tyr Asp Ser His
        115                 120                 125

Tyr Gln Gly Val Tyr Pro Val Lys Cys Asn Gln Asp Arg Phe Ile Ile
    130                 135                 140

Glu Asp Ile Val Glu Phe Gly Ser Gly Phe Arg Phe Gly Leu Glu Ala
145                 150                 155                 160

Gly Ser Lys Pro Glu Ile Leu Leu Ala Met Ser Cys Leu Cys Lys Gly
                165                 170                 175

Asn Pro Glu Ala Phe Leu Val Cys Asn Gly Phe Lys Asp Ser Glu Tyr
            180                 185                 190

Ile Ser Leu Ala Leu Phe Gly Arg Lys Leu Glu Leu Asn Thr Val Ile
        195                 200                 205

Val Leu Glu Gln Glu Glu Glu Leu Asp Leu Val Ile Asp Leu Ser Gln
    210                 215                 220

Lys Met Asn Val Arg Pro Val Ile Gly Leu Arg Ala Lys Leu Arg Thr
225                 230                 235                 240

Lys His Ser Gly His Phe Gly Ser Thr Ser Gly Glu Lys Gly Lys Phe
                245                 250                 255

Gly Leu Thr Thr Val Gln Ile Leu Arg Val Val Arg Lys Leu Ser Gln
            260                 265                 270

Val Gly Met Leu Asp Cys Leu Gln Leu Leu His Phe His Ile Gly Ser
        275                 280                 285

Gln Ile Pro Ser Thr Ala Leu Leu Ser Asp Gly Val Ala Glu Ala Ala
    290                 295                 300
```

```
Gln Leu Tyr Cys Glu Leu Val Arg Leu Gly Ala His Met Lys Val Ile
305                 310                 315                 320

Asp Ile Gly Gly Gly Leu Gly Ile Asp Tyr Asp Gly Ser Lys Ser Gly
            325                 330                 335

Glu Ser Asp Leu Ser Val Ala Tyr Ser Leu Glu Glu Tyr Ala Ala Ala
            340                 345                 350

Val Val Ala Ser Val Arg Phe Val Cys Asp Gln Lys Ser Val Lys His
            355                 360                 365

Pro Val Ile Cys Ser Glu Ser Gly Arg Ala Ile Val Ser His His Ser
370                 375                 380

Val Leu Ile Phe Glu Ala Val Ser Ala Gly Gln Gln His Glu Thr Pro
385                 390                 395                 400

Thr Asp His Gln Phe Met Leu Glu Gly Tyr Ser Glu Val Arg Gly
                405                 410                 415

Asp Tyr Glu Asn Leu Tyr Gly Ala Ala Met Arg Gly Asp Arg Glu Ser
                420                 425                 430

Cys Leu Leu Tyr Val Asp Gln Leu Lys Gln Arg Cys Val Glu Gly Phe
            435                 440                 445

Lys Glu Gly Ser Leu Gly Ile Glu Gln Leu Ala Gly Val Asp Gly Leu
450                 455                 460

Cys Glu Trp Val Ile Lys Ala Ile Gly Ala Ser Asp Pro Val Leu Thr
465                 470                 475                 480

Tyr His Val Asn Leu Ser Val Phe Thr Ser Ile Pro Asp Phe Trp Gly
                485                 490                 495

Ile Asp Gln Leu Phe Pro Ile Val Pro Ile His Lys Leu Asp Gln Arg
            500                 505                 510

Pro Ala Ala Arg Gly Ile Leu Ser Asp Leu Thr Cys Asp Ser Asp Gly
            515                 520                 525

Lys Ile Asn Lys Phe Ile Gly Gly Glu Ser Ser Leu Pro Leu His Glu
530                 535                 540

Met Asp Asn Asn Gly Cys Ser Gly Gly Arg Tyr Tyr Leu Gly Met Phe
545                 550                 555                 560

Leu Gly Gly Ala Tyr Glu Glu Ala Leu Gly Gly Val His Asn Leu Phe
                565                 570                 575

Gly Gly Pro Ser Val Val Arg Val Leu Gln Ser Asp Gly Pro His Gly
            580                 585                 590

Phe Ala Val Thr Arg Ala Val Met Gly Gln Ser Ser Ala Asp Val Leu
            595                 600                 605

Arg Ala Met Gln His Glu Pro Glu Leu Met Phe Gln Thr Leu Lys His
610                 615                 620

Arg Ala Glu Glu Pro Arg Asn Asn Asn Lys Ala Cys Gly Asp Lys
625                 630                 635                 640

Gly Asn Asp Lys Leu Val Val Ala Ser Cys Leu Ala Lys Ser Phe Asn
            645                 650                 655

Asn Met Pro Tyr Leu Ser Met Glu Thr Ser Thr Asn Ala Leu Thr Ala
            660                 665                 670

Ala Val Asn Asn Leu Gly Val Tyr Tyr Cys Asp Glu Ala Ala Ala Gly
            675                 680                 685

Gly Gly Gly Lys Gly Lys Asp Glu Asn Trp Ser Tyr Phe Gly
            690                 695                 700
```

<210> SEQ ID NO 3
<211> LENGTH: 19
<212> TYPE: DNA

```
<213> ORGANISM: Artificial
<220> FEATURE:
<223> OTHER INFORMATION: direct-sense primer for amplifying genomic ADC1
      DNA from Arabidopsis

<400> SEQUENCE: 3
atgcctgctc tagcttttg                                                    19

<210> SEQ ID NO 4
<211> LENGTH: 19
<212> TYPE: DNA
<213> ORGANISM: Artificial
<220> FEATURE:
<223> OTHER INFORMATION: reverse-sense primer for amplifying genomic
      ADC1 DNA from Arabidopsis

<400> SEQUENCE: 4
accgaaataa gaccaattc                                                    19

<210> SEQ ID NO 5
<211> LENGTH: 21
<212> TYPE: DNA
<213> ORGANISM: Artificial
<220> FEATURE:
<223> OTHER INFORMATION: direct-sense primer for the quantitative
      determination of ADC1 mRNA

<400> SEQUENCE: 5
gtggtgataa ggggaacgac a                                                 21

<210> SEQ ID NO 6
<211> LENGTH: 25
<212> TYPE: DNA
<213> ORGANISM: Artificial
<220> FEATURE:
<223> OTHER INFORMATION: reverse-sense primer for the quantitative
      determination of ADC1 mRNA

<400> SEQUENCE: 6
caaccgaaat aagaccaatt ctcat                                             25

<210> SEQ ID NO 7
<211> LENGTH: 24
<212> TYPE: DNA
<213> ORGANISM: Artificial
<220> FEATURE:
<223> OTHER INFORMATION: direct-sense primer for the quantitative
      determination of Actin2 mRNA

<400> SEQUENCE: 7
gattcagatg cccagaagtc ttgt                                              24

<210> SEQ ID NO 8
<211> LENGTH: 20
<212> TYPE: DNA
<213> ORGANISM: Artificial
<220> FEATURE:
<223> OTHER INFORMATION: reverse-sense primer for the quantitative
      determination of Actin2 mRNA

<400> SEQUENCE: 8
tggattccag cagcttccat                                                   20

<210> SEQ ID NO 9
<211> LENGTH: 20
<212> TYPE: DNA
<213> ORGANISM: Artificial Sequence
```

```
<220> FEATURE:
<223> OTHER INFORMATION: direct-sense primer for amplifying DNA from
      promoter CaMV35S fused to ADC1 gene from Arabidopsis in tobacco

<400> SEQUENCE: 9
ggcttacgca gcaggtctca                                                    20

<210> SEQ ID NO 10
<211> LENGTH: 20
<212> TYPE: DNA
<213> ORGANISM: Artificial Sequence
<220> FEATURE:
<223> OTHER INFORMATION: reverse-sense primer for amplifying DNA from
      promoter CaMV35S fused to ADC1 gene from Arabidopsis in tobacco

<400> SEQUENCE: 10
tccgactccc ccgatttaga                                                    20

<210> SEQ ID NO 11
<211> LENGTH: 20
<212> TYPE: DNA
<213> ORGANISM: Artificial Sequence
<220> FEATURE:
<223> OTHER INFORMATION: direct-sense primer for the quantitative
      determination of ADC1 mRNA from Arabidopsis in tobacco transgenic
      plants

<400> SEQUENCE: 11
agaagctggt tccaagcctg                                                    20

<210> SEQ ID NO 12
<211> LENGTH: 19
<212> TYPE: DNA
<213> ORGANISM: Artificial Sequence
<220> FEATURE:
<223> OTHER INFORMATION: reverse-sense primer for the quantitative
      determination of ADC1 mRNA from Arabidopsis in tobacco transgenic
      plants

<400> SEQUENCE: 12
gctttcacga tcaccacgc                                                     19

<210> SEQ ID NO 13
<211> LENGTH: 20
<212> TYPE: DNA
<213> ORGANISM: Artificial Sequence
<220> FEATURE:
<223> OTHER INFORMATION: direct-sense primer for the quantitative
      determination of Actin2 mRNA in tobacco

<400> SEQUENCE: 13
cattggcgct gagagattcc                                                    20

<210> SEQ ID NO 14
<211> LENGTH: 19
<212> TYPE: DNA
<213> ORGANISM: Artificial Sequence
<220> FEATURE:
<223> OTHER INFORMATION: reverse-sense primer for the quantitative
      determination of Actin2 mRNA in tobacco

<400> SEQUENCE: 14
gcagcttcca ttccgatca                                                     19

<210> SEQ ID NO 15
```

```
<211> LENGTH: 20
<212> TYPE: DNA
<213> ORGANISM: Artificial Sequence
<220> FEATURE:
<223> OTHER INFORMATION: direct-sense primer for amplifying ADC1 DNA
      from Arabidopsis in tomato

<400> SEQUENCE: 15
ccagcttctg cattttcaca                                                    20

<210> SEQ ID NO 16
<211> LENGTH: 20
<212> TYPE: DNA
<213> ORGANISM: Artificial Sequence
<220> FEATURE:
<223> OTHER INFORMATION: reverse-sense primer for amplifying ADC1 DNA
      from Arabidopsis in tomato

<400> SEQUENCE: 16
ccattgttgt ccatctcgtg                                                    20
```

PLANT HAVING RESISTANCE TO LOW-TEMPERATURE STRESS AND METHOD OF PRODUCTION THEREOF

CROSS-REFERENCE TO RELATED APPLICATIONS

The present application is a 35 USC §371 National Phase filing of PCT Application Number PCT/ES2009/000363, filed 10 Jul. 2009, which claims priority from the Spanish Patent Application No. P200802145, dated 11 Jul. 2008, entitled "Plant having resistance to low-temperature stress and method of production thereof" the subject matter of which is hereby being specifically and entirely incorporated herein by reference for all that it discloses and teaches.

The present invention relates to plants having improved resistance to low temperatures. The present invention further relates a method of producing such plants.

BACKGROUND ART

Plants adapt to various types of environmental stress such as the temperature of their habitats. However, in terms of temperature stress, for example, plants are susceptible to hot or cold temperatures when exposed to environments over or under the maximum or minimum optimum growth temperature, leading to impairment upon the gradual or sudden loss of the physiological functions of cells.

Efforts have been made to expand the temperature adaptability of plants by breeding means such as selection or cross breeding in order to make use of wild plants adapted to various temperature environments for food crops, horticultural plants, and the like. The planting period in which vegetables, flowers and ornamental plants, fruit trees, and the like can be cultivated has been expanded by such breeding means as well as by protected horticulture.

Polyamines, the general term for aliphatic hydrocarbons with 2 or more primary amino groups, are ubiquitous natural substances in organisms, with more than 20 types discovered so far. Typical polyamines include putrescine, spermidine, and spermine. Known polyamine metabolism-related enzymes involved in the biosynthesis of said polyamines include arginine decarboxylase (ADC), ornithine decarboxylase (ODC), S-adenosylmethionine decarboxylase (SAMDC), spermidine synthase (SPDS), and spermine synthase (SPMS). The involvement of some of the polyamine metabolism-related enzymes in various types of environmental stress has recently been reported.

The European patent application EP 1.329.153 teaches that in plant tissues exhibiting cold stress resistance, the content of spermidine and spermine is increased. In this patent application it is exemplified that introducing the spermidine synthase gene into a plant, the spermidine and spermine levels are increased. When the transgenic plant was submitted to low temperature, it was confirmed that it has improved cold stress resistance.

The US patent application number 2006/0225154 teaches that spermidine, spermine and putrescine levels are increased when a plant is transformed with a spermidine gene synthase. This patent application states that low temperature stress defense effect can be imparted to the plant by introducing the spermidine synthase gene into the plant.

Regarding the use of the ADC gene for conferring cold stress resistance to plants, it is remarkable the fact that in the Brassicaceae family, the ADC gene appears to be duplicated, thus yielding two paralogues, generally called ADC1 and ADC2 (cf. Galoway et al., "Phylogenetic utility of the nuclear gene Arginine Decarboxylase: an example from Brassicaceae", Molecular Biology and Evolution, 1998, v. 15, p. 1312-1320). The different roles played by each one of the paralogues have been studied.

In Hummel I. et al. (cf. Hummel et al., "Differential gene expression of ARGININE DECARBOXYLASE ADC1 and ADC2 in *Arabidopsis thaliana*: characterization of transcriptional regulation during seed germination and seedling development", New Phytologist, 2004, v. 163, p. 519-531) the promoter activities of ADC1 and ADC2 were studied in stable transformants. In this report, it was found that chilling had a strong effect on ADC1 and ADC2 promoter activity. It was concluded that in *Arabidopsis* the polyamine response to chilling is shown to correlate with transcriptional activation of the ADC1 promoter.

In Alcazar et al. (Alcazar et al., "Overexpression of ADC2 in *Arabidopsis* induces dwarfism and late-flowering through GA deficiency", The Plant Journal, 2005, v. 43, p. 425-436) an *Arabidopsis* transgenic plant was generated. The transgenic plant overexpressed the ADC2 gene, given rise to an accumulation of putrescine, without affecting the levels of spermidine or spermine. Furthermore, the plants overexpressing ADC2 showed dwarfism and late-flowering.

Despite the efforts made in the prior art, the research of new plants with improved stress resistance and methods for their obtention are still an active field.

SUMMARY OF THE INVENTION

The inventors of the present invention have found that introducing into a plant an ADC1 gene sequence, the resulting transgenic plant shows low-temperature stress resistance. Furthermore, the phenotype of the transgenic plant does not differ from the wild type plant's phenotype, as it is illustrated below.

In Alcazar et al. (supra), it was described that over-expressing the ADC2 gene (the paralogue of ADC1 gene), the resulting transgenic plant suffered changes in its phenotype (such as dwarfism) and in its growth (late-flowering).

On the other hand, in Hummel I. et al. (supra) it is mentioned that the chilling effect was correlated to changes in mRNA level, and consistent with the specific presence of two copies of a low-temperature response element in the promoter of ADC1 and with the potential impact of the transposable element on gene expression, as a copy of this low-temperature-response element is part of the ADC1 transposable element.

Surprisingly, it has been found that the over-expression of ADC1 confers low-temperature stress resistance to the plant and does not affect the transgenic plant's phenotype or growth.

Furthermore, and as it is illustrated below, the low-temperature stress resistance is achieved by over-expressing the ADC1 gene, independently of the promoter used for its expression. As shown below, the construct used to introduce the ADC1 gene into the plant comprised a constitutive promoter other than the ortholog promoter of the gene. Then, the inventors of the present invention have found that the relevant fact in order to confer low-temperature stress resistance is the over-expression of the ADC1 gene, independently of whether the ADC1 ortholog promoter is present in the construct used for transfecting the plant.

On the other hand, the inventors have found that when the ADC1 gene is over-expressed into the plant: a) there is an accumulation of putrescine; b) the level of spermidine does not almost change; and c) the spermine level is reduced (levels compared with a wild-type plant). This finding contravenes the disclosures made in the prior art using other polyamine synthase gene (i.e., spermidine synthase gene), wherein the effects observed were based on an increase in spermidine and/or spermine as a consequence of the accumulation of putrescine, or a stable production of said polyamines.

Thus, in a first aspect the present invention refers to a method of producing plants with improved low-temperature stress resistance, comprising the step of transforming cells of a plant with an exogenous arginine decarboxylase ADC1 gene sequence under the control of a promoter capable of functioning in the plant.

Without being bound to the theory, it is believed that due to the different subcellular location of the ADC1, the resulting transgenic plants have not developmental alterations, being increased the productivity and yield, compared with those over-expressing ADC2.

In a second aspect, the present invention refers to a transformed plant obtainable by the method as defined according to the first aspect of the invention.

Throughout the description and claims the word "comprise" and variations of the word, such as "comprising", is not intended to exclude other technical features, additives, components, or steps. Additional objects, advantages and features of the invention will become apparent to those skilled in the art upon examination of the description or may be learned by practice of the invention. The following examples and drawings are provided by way of illustration, and is not intended to be limiting of the present invention.

DETAILED DESCRIPTION OF PARTICULAR EMBODIMENTS

Figure 1:
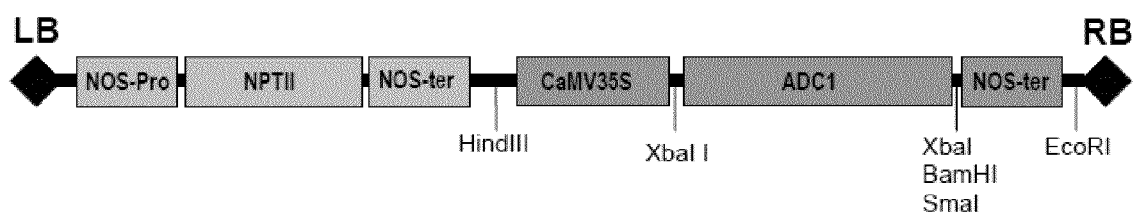
FIG. 1: Structure of the expression construct containing the putrescine biosynthesis gene ADC1 under the control of the constitutive promoter CaMV35S.
Figure 2:
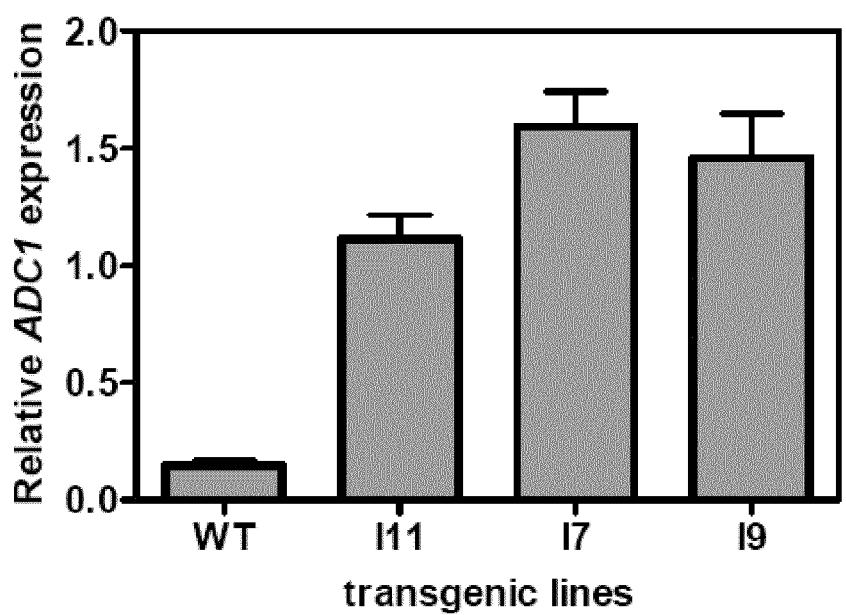
FIG. 2: Relative transcript levels of the putrescine biosynthetic gene ADC1 in transgenic (I11, I7, I9) and control (wt) plants.

In the present invention "plants with improved low-temperature stress resistance" are plants in which limited growth or damage caused by low-temperature stress during the growth of the plant can be avoided or diminished.

As used herein, "exogenous" means not intrinsic to the plant, but externally introduced. Accordingly, an "exogenous ADC1 gene sequence" may be an ADC1 enzyme gene homologous to the host plant (that is, derived from the host plant), which is externally introduced by genetic manipulation. The use of a host-derived ADC1 enzyme gene is preferred in consideration of the identity of the codon usage.

In one embodiment of the first aspect of the invention, the method further comprises the regeneration of the plant from the transformant cells containing the exogenous ADC1 gene sequence under the control of a promoter capable of functioning in plants.

The whole ADC1 gene sequence is available from the GenBank database with the reference gene ID 816149.

The arginine decarboxylase ADC1 gene coding sequence from *Arabidopsis thaliana* (SEQ ID NO: 1) is available through the GenBank database. Its accession number is NM_127204.

The arginine decarboxylase ADC1 amino acid sequence (SEQ ID NO: 2) is available through the GenBank database. Its accession number is Q9SI64.

In another embodiment of the first aspect of the invention, the exogenous arginine decarboxylase ADC1 gene sequence is selected from the group consisting of: a) a nucleotide sequence comprising the sequence SEQ ID NO: 1; b) a nucleotide sequence coding for an amino acid sequence comprising the sequence SEQ ID NO: 2; c) a nucleotide sequence which hybridizes with SEQ ID NO: 1 or a complementary sequence thereof under stringent conditions and encodes a protein having the arginine decarboxylase activity; and d) a nucleotide sequence coding for a protein with arginine decarboxylase activity, comprising the sequence (a) with one or more bases deleted, substituted, inserted or added. Preferably, the sequence corresponds to SEQ ID NO: 1.

The exogenous ADC1 gene sequence may be introduced into cells by any method of genetic engineering. Examples include protoplast fusion with heterologous plant cells having the ADC1 gene sequence, infection with a plant virus having a viral genome genetically manipulated to express the ADC1 enzyme gene, or transformation of host plant cells using an expression vector containing the ADC1 enzyme gene.

Examples of promoters capable of functioning in plants include the 35S promoter of the cauliflower mosaic virus (CaMV) which is structurally expressed in plant cells, the nopaline synthase gene (NOS) promoter, octopine synthase gene (OCS) promoter, phenylalanine ammonia lyase (PAL) gene promoter, and chalcone synthase (CHS) gene promoter. Other well-known plant promoters not limited to these are also available.

Not only promoters constitutively expressed in the entire organ such as the 35S promoter, but also promoters regulated by low temperature, stress, drought, light, heat, hormones, damage or the like can be used to express the target gene according to the living environment. For example, the ADC1 enzyme gene and a promoter capable of transcription only when the plant is exposed to low temperatures can be used to control the polyamine metabolism of the plant only at low temperatures and to improve the low-temperature stress resistance. An organ- or tissue-specific promoter can also be used to express the target gene only in specific organs or tissue.

When the exogenous ADC1 gene sequence is introduced by infection with *Agrobacterium tumefaciens*, the ADC1 enzyme gene expression cassette can be inserted in the T-DNA region (region transferred to plant chromosome) on a Ti or Ri plasmid of the cells. At present, binary vector systems are used in standard methods of transformation with *Agrobacterium*. Examples of commercially available binary vectors include pBI101 and pBI121 (both by Clontech). The Vir region involved in the incorporation of the T-DNA has trans action on the separate Ti (or Ri) plasmid referred to as the helper plasmid.

Various conventionally known methods can be used for the transformation of the plants. Examples include the PEG method in which protoplasts are isolated from plant cells by treatment with a cell wall-degrading enzyme such as cellulase or hemicellulase, and polyethylene glycol is added to a suspension of the protoplasts and an expression vector containing the aforementioned ADC1 enzyme gene expression cassette to incorporate the expression vector into the protoplasts by a process such as endocytosis; the liposome method in which an expression vector is introduced by ultrasonic treatment or the like into lipid membrane vesicles such as phosphatidylcholine, and the vesicles are fused with protoplasts in the presence of PEG; methods of fusion in a similar process using micelles; and electroporation in which electrical pulses are applied to a suspension of protoplasts and an expression vector to incorporate the vectors in the external solution into the protoplasts. However, these methods are complicated in that they require a culturing technique for the redifferentiation of the protoplasts into plants. Processes for introducing the gene into intact cells with cell walls include direct injection such as microinjection in which a micropipette is inserted into cells to inject the vector DNA under hydraulic or gas pressure into the cells, or the particle gun method in which metal microparticles coated with DNA are accelerated through the detonation of an explosive or gas pressure and thus introduced into the cells, and methods involving the use of infection with *Agrobacterium*. Drawbacks of microinjection are the need for considerable training and the small number of cells that are handled. It is therefore more desirable to transform plants with more convenient methods such as the *Agrobacterium* method and the particle gun method. In the particle gun method, minute metal (usually gold) beads coated with the DNA of interest are directly shot into plant cell. The particle gun method is useful in that genes can be directly introduced into the apical meristem of plants while cultivated. *Agrobacterium tumefaciens* is a soil bacterium which contains, as well as its chromosome, and extra circular mini-chromosome, called the tumor inducing plasmid (Ti). Part of the Ti plasmid is transferred onto the chromosomes of the host plant where it becomes integrated (T-DNA). Several gene loci of the bacterial chromosome and a set of virulence genes (vir) located on the Ti plasmid code for functions involved in plant cell recognition and attachment as well as for the excision, transfer and integration of the T-DNA into the plant genome. In general, the *Agrobacterium* method is considered preferable to the gene gun, because of the greater frequency of single-site insertions of the foreign DNA, making it easier to monitor.

Illustrative non-limitative examples of plant cells which can be transformed with the exogenous ADC1 gene according to the first aspect of the invention, are the cells derived from: callus, seeds, leaves, stems, vines, roots, root tubers or stem tubers, flowers and the like.

Examples of plants which may be transformed with the process according to the first aspect of the invention include, but are not limited to, dicotyledons, monocotyledons, herbaceous plants, and shrubs. Examples include sweet potatoes, tomatoes, cucumbers, squash, melons, watermelon, tobacco (*Nicotinia tabacum*), *Arabidopsis thaliana*, bell peppers, eggplant, beans, taro, spinach, carrots, strawberries, white potatoes, rice, corn, alfalfa, wheat, barley, soybeans, rapeseed, *sorghum*, *Eucalyptus*, poplar, kenaf, *Eucommia ulmoides*, sugarcane, sugar beet, cassaya, sago palm, *Chenopodium album*, lilies, orchids, carnations, roses, *chrysanthemum*, petunias, *Torenia fournieri*, antirrhinum, cyclamen, gypsohila, geranium, sunflowers, *Zoisia japonica*, cotton, matsutake mushrooms, shiitake mushrooms, mushrooms, ginseng, citrus fruits, bananas, and kiwi fruit.

The "base sequences with one or more bases deleted, substituted, inserted, or added" referred to here are widely known by those having ordinary skill in the art to sometimes retain physiological activity even when the amino acid sequence of a protein generally having that physiological activity has one or more amino acids substituted, deleted, inserted, or added. Genes that have such modifications and that code for an ADC1 enzyme are included within the scope of the present invention. However, it is essential that such modifications do not result in the loss of activity of said enzyme.

The "stringent conditions" referred to here mean conditions under which only base sequences coding for a polypeptide with ADC1 activity equivalent to the ADC1 enzyme gene encoded by a specific ADC1 enzyme gene sequence form hybrids with the specific sequence (referred to as specific hybrids), and base sequences coding for polypeptides with no such equivalent activity do not form hybrids with the specific sequence (referred to as non-specific hybrids). One with ordinary skill in the art can readily select such conditions by varying the temperature during the hybridization reaction and washing process, the salt concentration during the hybridization reaction and washing process, and so forth.

EXAMPLES

Example 1

Obtention of Transgenic *Arabidopsis* Plants

A. Plasmid Construction

The *Arabidopsis* ADC1 cDNA was amplified by PCR from genomic DNA with the following primers: forward 5'-ATGCCTGCTCTAGCTTTTG-3' (SEQ ID NO: 3), and reverse 5'-ACCGAAATAAGACCAATTC-3' (SEQ ID NO: 4). The amplified DNA fragment was cloned into pGEM (Stratagene, Heidelberg) and checked by sequencing. The construct containing the ADC1 cDNA, flanked by the cauliflower mosaic virus constitutive promoter (CaMV35S) and the nopaline synthase (NOS) terminator, in a binary vector (pBI121-ADC1) was obtained by replacing the SmaI/SacI GUS gene in pBI121 (cf. Chen et al., "Complete sequence of the binary vector pBI121 and its application in cloning t-DNA insertion from transgenic plants", Molecular Breeding, 2003, v. 11, p. 289-293; accession number AF485783) with a XbaI/XbaI fragment of ADC1 cDNA (2.6 kb). This construct was introduced into *Agrobacterium tumefaciens* C58C1 via electroporation and used to transform different plant species as explained below.

B. *Arabidopsis thaliana* Transformation

*Arabidopsis thaliana* Col0 plants were transformed with *A. tumefaciens* containing the pBI121-ADC1 construct by floral dipping (cf. Clough S. J. et al., "Floral dip: a simplified method for *Agrobacterium*-mediated transformation of *Arabidopsis thaliana*", Plant J., 1998, v. 16, p. 735-743). The seeds were collected from the dipped plants and selected in Murashige and Skoog culture medium, hereinafter abbreviated as "MS" (cf. Murashige T. et al., "A revised medium for rapid growth and bioassays with tobacco tissue culture", Physiol. Plant., 1962, v. 15, p. 473-497) containing 50 mg/l of kanamycin as an antibiotic for the selection of transformants. The progeny of the kanamycin resistant plants was analyzed for kanamycin resistance segregation. Seeds of plants with a 3:1 segregation ratio were further cultivated and the resulting progeny was again analyzed for segregation of kanamycin resistance to identify plants homozygous for the T-DNA insert. Three homozygous lines (I7, I9 and I11) were selected for further analysis.

C. Characterization of Transgenic Plants

C.1. Estimation of ADC1 mRNA by Real-Time RT-PCR

Total RNA was obtained from the entire aerial part of 4-week old *Arabidopsis thaliana* non transformed plants (wt) and transformed with the pBIADC1 plasmid (I7, I9, I11) using the TRIzol reagent (Invitrogen, Carlsbad, Calif.). One microgram of total RNA was treated with amplification grade DNase (Invitrogen) to eliminate genomic DNA contamination. First-strand cDNA was synthesized with random hexamers using SuperScript III first-strand synthesis system according to the manufacturer's instructions (Invitrogen). Real-time RT-PCR with the SYBR Green I dye method was performed using the first-strand cDNA as a template on a sequence detector system (model 7700; Applied Biosystems, Foster, Calif.). The amplification efficiency of every sample under analysis was performed using DART-PCR datasheet (cf. Peirson S. N. et "Experimental validation of novel and conventional approaches to quantitative real-time PCR data analysis", Nucleic Acids Res., 2003, v. 31, e73), which uses a simple algorithm (cf. Tichopad A. et al., "Standardized determination of real-time PCR efficiency from a single reaction set-up", Nucleic Acids Res., 2003, v. 31, e122.) and fluorescence raw data that allows comparable results to be obtained without a need for standard curves. Amplification efficiencies were calculated for every single reaction from its amplification profile and were tested to detect anomalous samples (outliners) and differences between groups (amplification equivalence) by ANOVA using the same DART-PCR datasheet. The mean starting fluorescence ($R_0$) obtained from the mean efficiency was normalized using Actin2 mRNA as internal control in every experiment. These analyses were performed twice in independent experiments with very similar results. The following gene-specific primer sets were used: ADC1 (forward: 5'-GTGGTGATAAGGGGAAC-GACA-3' (SEQ ID NO: 5), reverse: 5'-CAACCGAAATAA-GACCA-ATTCTCAT-3' (SEQ ID NO: 6)), and Actin2 (forward: 5'-GATTCAGATGCCCAGAAGTCTTGT-3' (SEQ ID NO: 7), reverse: 5'-TGGATTCCAGCAGCTT-CCAT-3' (SEQ ID NO: 8)).

C.2. Polyamine Analysis

Polyamines (PAs) were analyzed by high-performance liquid chromatography (HPLC) separation of dansyl chloride-derivatized PAs. The extraction and determination methods have been described previously (cf. Marcè M. et al., "Rapid high-performance liquid chromatographic method for quantitation of polyamines as their dansyl derivatives: Application to plant and animal tissues", J. Chromatogr. B. Biomed. Appl., 1995, v. 666, p. 329-33).

Figure 3:
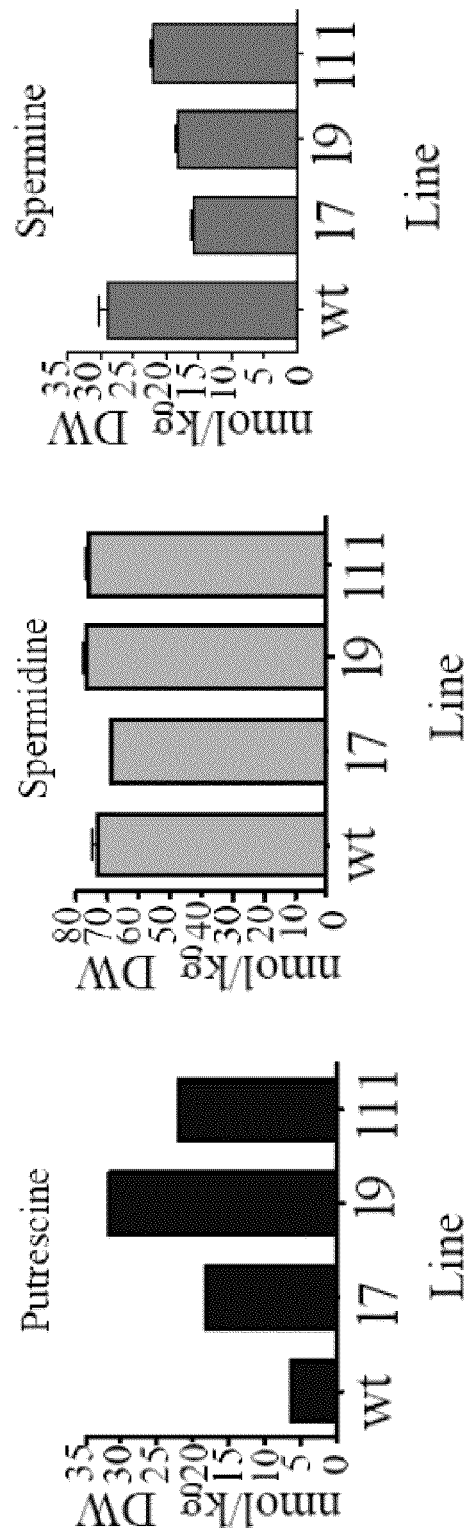
FIG. 3: Polyamine levels in *Arabidopsis* wild type (wt) and transgenic plants over-expressing ADC1 (I7, I9, I11).
Figure 4:
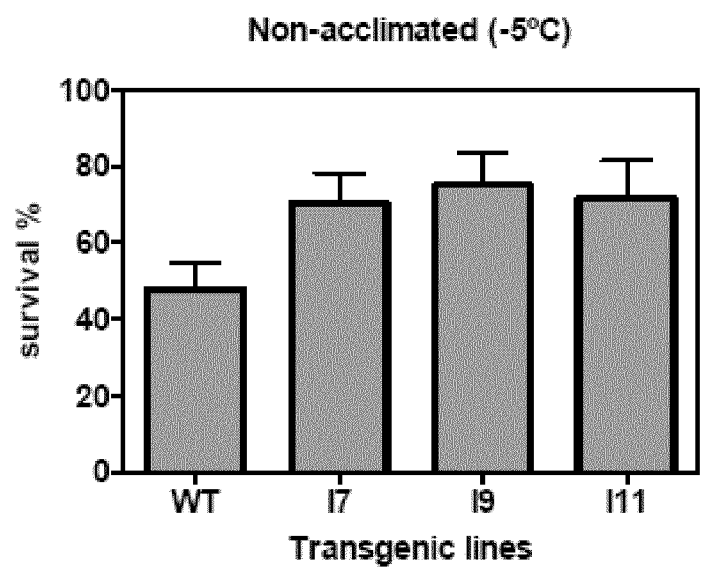
FIG. 4: Freezing resistance of wild-type and transgenic plants. Three-week old plants were exposed to different freezing temperatures for 6 hours: (A) −5° C. (non-acclimated), and (B) −12° C. (cold-acclimated). Freezing resistance was estimated as the percentage of plants surviving each specific temperature after 14 days of recovery under unstressed conditions.
Figure 4:
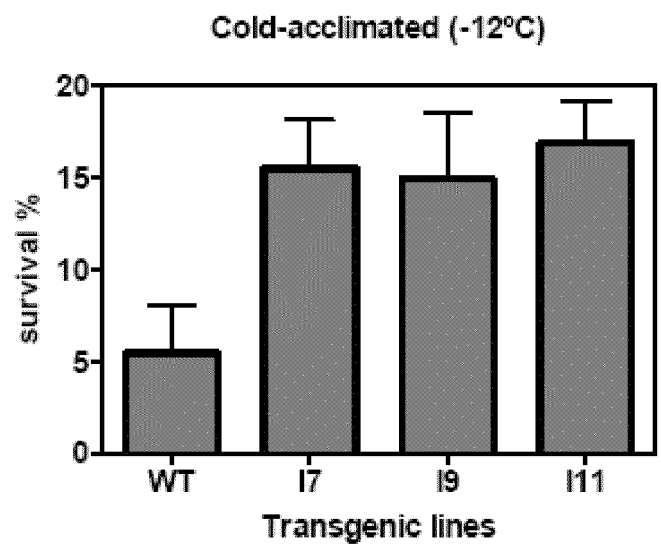

As it is shown in FIG. 3, the putrescine levels in the transgenic plants are increased, whereas the spermidine is not affected and the spermine level is reduced. From the results obtained, it can be concluded that the over-expression of ADC1 increases the accumulation of putrescine.

C.3. Freezing Assays

Three-week-old plants (wt, I1, I9, I11) were used in this assay. To obtain the plants, seeds were sown in pots containing a mixture of soil and vermiculite (3:1 v/v), irrigated with water and Hoagland's based mineral solution, and grown at 21±1° C. under neutral-day photoperiods (12 hours of cool-white fluorescent light, photon flux of 70-90 µmol m$^{-2}$ sec$^{-1}$).

Low-temperature treatments were performed by transferring plants to a growth chamber set to 4±1° C. for different periods of time under the light and photoperiodic conditions described above.

Freezing assays were carried out in a temperature programmable freezer. Non-acclimated or cold-acclimated (7 days, 4° C.) 3-week-old-plants were exposed to 4° C. for 30 min in darkness and subsequently the temperature was lowered at 2° C. per hour. The final freezing temperature (−5° C. for non-acclimated, and −11° C. for cold-acclimated) was maintained for 6 hours, and then the temperature was increased again to 4° C. at the same rate. After thawing at 4° C. for 12 hours in the dark, plants were returned to their original growth conditions (see above). Resistance to freezing was determined as the capacity of plants to resume growth after 14 days of recovery under control conditions.

As it is derived from the results obtained, the transgenic plants over-expressing the exogenous ADC1 gene are more resistant to low-temperature stress showing, at the same time, the same phenotype traits as the wild-type plant.

Example 2

Obtention of Transgenic Tobacco Plants

Leaf discs of tobacco plants (*Nicotiana tabacum* cv. Burley 21) are transformed with *Agrobacterium tumefaciens* LBA4404 harbouring the construct of interest as described by Horsch et al. (cf. R. B. Horsch et al., "A simple and general method for transferring genes into plants" Science 1985, vol. 227, pp. 1229-1231). The shooting medium contains MS salt mixture (Duchefa, ND), B5 Gamborg vitamins (Duchefa), 1 mg/l benzyladenine (BA, Sigma), 0.1 mg/l naphthalene acetic acid (NAA, Sigma), 50 mg/l kanamycin as antibiotic for the selection of transformed cells and 100 mg/l Claforan to avoid *A. tumefaciens* growth. After 6-7 weeks in this medium, shoots of the adequate size to be transferred to rooting medium are obtained. Regenerated shoots are excised and transferred to rooting medium: MS with 50 mg/l kanamycin but without hormones (BA, NAA). The kanamycin-resistant plants (3-10 cm hogh) are transferred to compost substrate and grown in the glasshouse. After 3 months the plants are flowering and self pollination is achieved covering an entire stand of flowers and buds with a paper bag. One month later the seeds are usually mature and can be used for germination. These seeds are analyzed for kanamycin resistance segregation, and the plants that are able to grow in the presence of kanamycin are used for further analysis.

The expression levels of ADC1 in the transgenic plants, as well as putrescine levels, are determined in the aerial part of 4-week old tobacco plants as described in the *Arabidopsis* protocol.

The freezing resistance of 3 transgenic lines selected for their high putrescine levels is determined as described for *Arabidopsis*.

Example 3

Obtention of Transgenic Tobacco Plants

A. *Nicotiana tabacum* Transformation

The pBI121-ADC/plasmid described in example 1 was introduced into *Agrobacterium tumefaciens* LBA4404 by the freezing transformation method. Agrobacteria were grown at 28° C. with shaking (200 rpm) in YEB broth containing 100 µg/ml streptomycin, 100 µg/ml rifampycin and 50 µg/ml kanamycin. Bacterial suspension of $OD_{600}$=0.80 was used for transformation. Transgenic tobacco plants (*Nicotiana tabacum* cv. Xanthi) were generated by the standard leaf disc transformation procedure (cf. Horsch et al. supra). Leaf discs (0.5×0.5 $cm^2$) from sterile tobacco plants were soaked in *Agrobacterium* containing pBI121-ADC1 construct for 5-10 min with occasional shaking. The *Agrobacterium*-infected leaf discs were cultivated on MS medium at 25° C. for 2 days and transferred to shooting medium, which contains MS salt mixture (Duchefa, ND), B5 Gamborg vitamins (Duchefa), 1 mg/l benzylaminopurine (BAP, Sigma), 0.1 mg/l naphthalene acetic acid (NAA, Sigma), 100 mg/l kanamycin as antibiotic for the selection of transformed cells and 250 mg/l Claforan to avoid *A. tumefaciens* growth. After 7-8 weeks in this medium, the regenerated shoots were of a suitable size to be excised and transferred to rooting medium: MS with 100 mg/l kanamycin but without hormones (BAP, NAA).

The kanamycin-resistant plants (5-10 cm high) were transferred to compost substrate and grown in the greenhouse ($T_0$ plants). After 4-5 months the plants were flowering and self pollination was achieved by covering an entire stand of flowers and buds with a paper bag. About one month later the seeds were usually mature and could be used for germination. These seeds were analyzed for kanamycin resistance segregation, and the plants that were able to grow in the presence of kanamycin were used for further analysis ($T_1$ plants).

Genomic DNA was extracted from 5 to 6 week-old $T_0$ transgenic plants, using the Qiagen DNeasy Plant Mini kit, and around 50 ng of DNA was used for PCR. Putative transgenic plants were confirmed by amplifying the genomic DNA with 35S-F (5'-GGCTTACGCAGCAGGTCTCA-3', SEQ ID NO: 9) as the sense primer designed against the CaMV 35S promoter region and ADC1-R (5'-TCCGACTCCCCCGATT-TAGA-3', SEQ ID NO: 10) as the antisense primer, designated against the ADC1 ORF.

Figure 5:
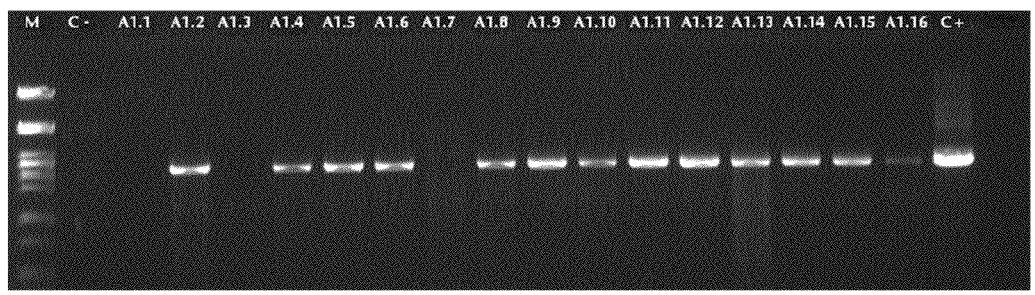
FIG. 5: PCR analysis of tobacco genomic DNA prepared from wild-type (C−) and regenerated kanamycin-resistant shoots. M λ-PstI digested DNA markers, C+ plasmid pBI121-ADC1, A1.1-A1.16 kanamycin-resistant lines.

A total of 11 independent transgenic lines were obtained from the screening of kanamycin-resistant regenerated plants and PCR detection (FIG. 5). The progeny of these plants was analyzed for kanamycin resistance segregation. Seeds of plants with a 3:1 segregation ratio, that are supposed to have only one insertion of the transgene, were further cultivated and used for analysis.

B. Characterization of Transgenic Plants

B.1. Estimation of ADC1 Expression Level by Semi Quantitative RT-PCR

Total RNA was isolated from the leaves of 3-week old *N. tabacum* plants, transformed or not with the pBI121-ADC1 plasmid, using the Trizol reagent (Invitrogen) and treated with RNase-Free DNAse (Invitrogen). Two micrograms of total RNA were used for cDNA synthesis using the Superscript III first-strand synthesis kit (Invitrogen) with random hexamers, at a final volume of 25 µl. PCR amplifications were performed taking 1 µl of cDNA solution in a 20 µl total volume reaction containing 0.25 mM of each dNTP, 1× reaction buffer, 0.5 U of Taq DNA polymerase (Takara) and 0.5 µM of the appropriate pair of primers: AtADC1 (forward: 5'-AGAAGCTGGTTCCAAGCCTG-3' SEQ ID NO: 11, reverse: 5'-GCTTTCACGATCACCACGC-3' SEQ ID NO: 12) and NtActin (forward: 5'-CATTGGCGCTGAGAGAT-TCC-3' SEQ ID NO: 13, reverse: 5'-GCAGCTTCCATTC-CGATCA-3' SEQ ID NO: 14). PCR conditions for amplification consisted of initial denaturation at 95° C. for 5 min, followed by 35 cycles of 95° C./30 sec, 62° C./30 sec and 72° C./2 min, and finally 10 min extension at 72° C. The PCR products were separated on 1.5% agarose gel electrophoresis, stained with ethidium bromide and visualized under UV. Expression was normalized using NtActin as internal control (FIG. 6).

Figure 6:
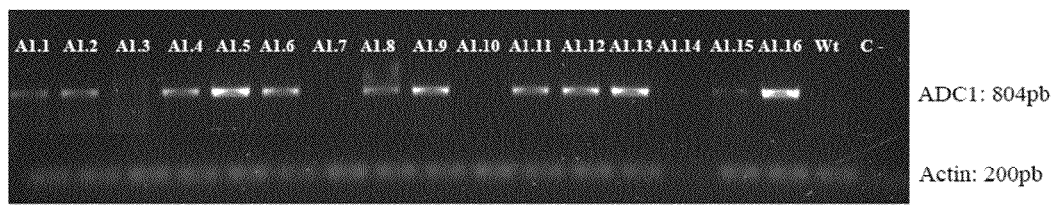
FIG. 6: Reverse transcriptase (RT-PCR) analysis of *Arabidopsis* ADC1 transcript in transgenic tobacco $T_0$ plants. Specific ADC1 and Actin primers were used.

The *Arabidopsis* ADC1 gene was expressed in the transgenic lines, although the expression level varied to some extent (FIG. 6). No significant abnormal morphological and growth/development phenotypes were observed in the tobacco plants over-expressing the *Arabidopsis* ADC1 gene. Independent transgenic lines A1.6, A1.13 and A1.16 were chosen for further studies as these lines showed high level of ADC/expression.

B.2 Polyamine Analysis

Figure 7:
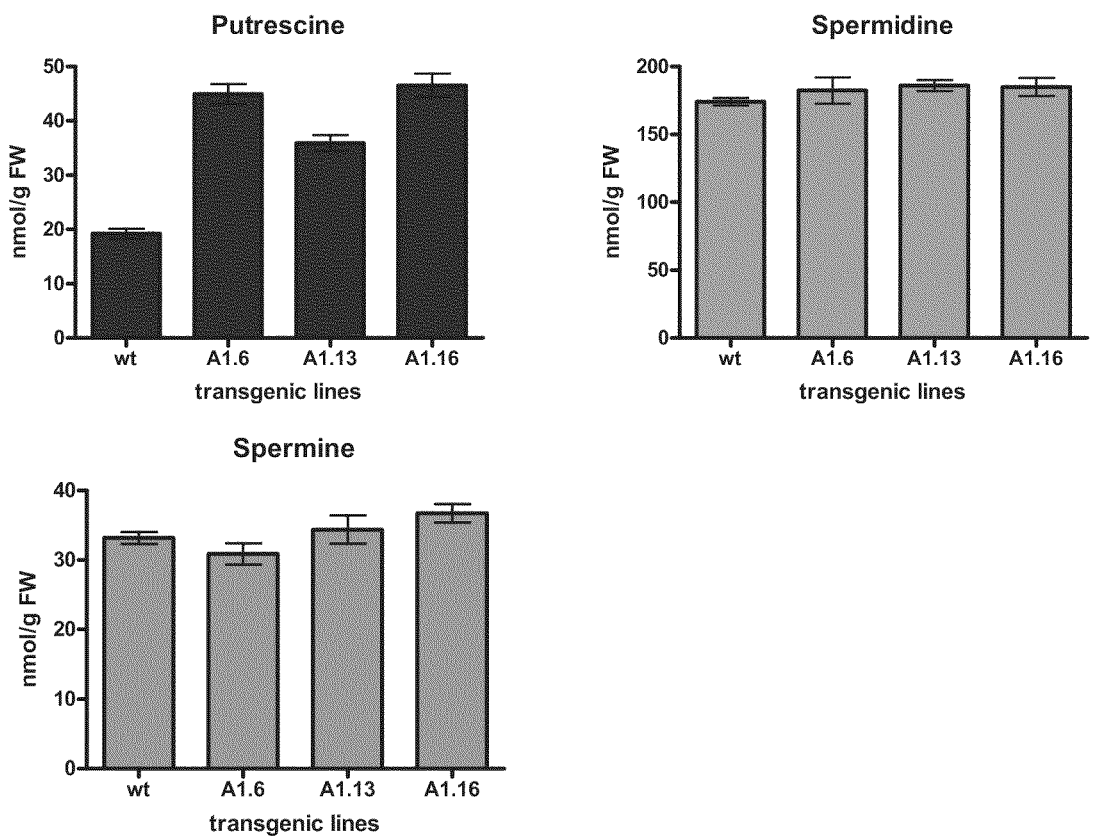
FIG. 7: Polyamine levels in tobacco wild-type (wt) and transgenic plants over-expressing *Arabidopsis* ADC1 gene (A1.6, A1.13, A1.16).

PA levels were determined in the aerial part of 4-week old tobacco plants from the $T_1$ generation as described in the *Arabidopsis* protocol (section C.2). Since this is not a homogeneous population, a mix of several plants (about 50) was used for polyamine extraction and quantification. As it is shown in FIG. 7, putrescine levels in the transgenic lines were higher than in the control, while no significant differences are observed in the levels of spermidine and spermine. From the obtained results it can be concluded that in tobacco the over-expression of *Arabidopsis* ADC1 induces the accumulation of putrescine.

B.3 Freezing Tolerance Assays

The freezing tolerance of 3 transgenic lines selected for their high expression of *Arabidopsis* ADC1 (A1.6, A1.13, A1.16) was determined in a similar way to that described for *Arabidopsis* (section C.3), but at different temperature. Three-week-old plants grown at 24±1° C. under long-day photoperiod (16 hours light/8 hours dark) were exposed to 4° C. for 30 min in the dark and subsequently the temperature was lowered 2° C. per hour until −3° C. The freezing temperature was maintained for 4 hours, and then was increased again to 4° C. After 12 h at 4° C. plants were returned to the original growth conditions, and the plants able to resume growth after two weeks were considered as resistant.

Figure 8:
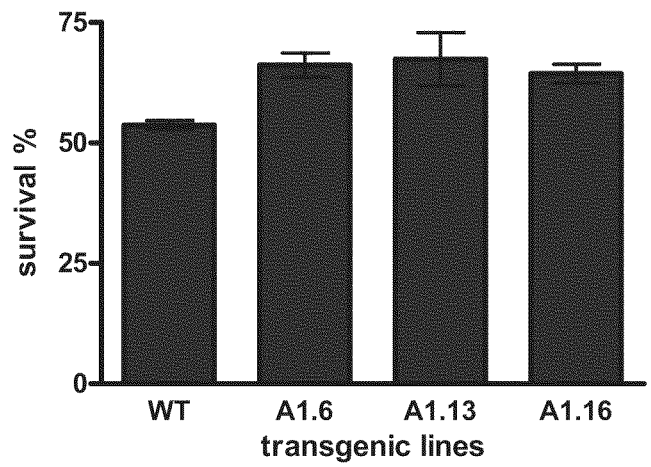
FIG. 8: Freezing resistance of wild-type and transgenic tobacco plants. Three-week old plants were exposed to −3° C. for 4 h. Freezing resistance was estimated as the percentage of plants surviving after 14 days of recovery under unstressed conditions.

As it is derived from the obtained results (FIG. 8), the transgenic tobacco plants over-expressing the *Arabidopsis*

ADC1 gene are more resistant to freezing stress than the control, and they present the same phenotype traits than the wild type plants. The survival percentage in the transgenic lines is 10-14% higher than in the control plants.

As mentioned in section B.2 these assays were performed with plants from the T1 generation, for this reason a big amount of plants was analyzed, that means 6 independent experiments with 40-50 plants of each line per experiment. Thus, these results are the mean of about 250 plants per line. More significant differences are expected when a homogeneous plant population (homozygous plants) is used. In the case of tobacco no differences in freezing tolerance were observed between acclimated and non-acclimated plants.

Example 4

Obtention of Transgenic Tomato Plants

A. *Licopersicum sculentum* Transformation

The pBI121-ADC1 plasmid was introduced into *Agrobacterium tumefaciens* LBA4404 by the freezing transformation method. A single colony of transformed *A. tumefaciens* was inoculated into 3 ml of AB medium containing 100 μg/ml streptomycin, 100 μg/ml rifampycin and 50 μg/ml kanamycin. After 8 h incubation at 28° C. with shaking (180 rpm), 1 ml of the bacteria culture was grown overnight, under the same conditions, in 50 ml of AB medium containing the antibiotics mentioned above and 2% glucose. After that, the bacterial suspension was centrifuged at 3000 rpm for 15 min at room temperature and the pellet, re-suspended in MSO at $OD_{600}$=0.6 final concentration, used for plant transformation.

Cotyledons of 10- to 12-day old tomato seedlings (*Licopersicum sculentum* cv. UC82) growing in vitro were used for transformation. The cotyledons were cut in two or three transversal pieces and floated upside down into *Agrobacterium tumefaciens* containing the pBI121-ADC1 construct diluted solution. After 10 min the explants were removed and blotted upside down directly on sterile Whatman filter paper placed directly on the top the GCF10 medium containing 375 μM acetosyringone into Petri dishes and returned to growth room at the dark for approximately 48 hours. After 48 h co-cultivation, the cotyledons were transferred to GCF10 medium containing 500 μg/ml carbenicillin and 40 μg/ml kanamycin. Cotyledons were placed upside down. Green calli or shoots were seen after 3 weeks incubation showing that the transformation was successful. The green calli were transferred to GCF11 medium containing 250 μg/ml carbenicillin and 40 μg/ml kanamycin.

After eight weeks of cultivation the shoots were transferred for rooting into TRI2 medium supplemented with 250 μg/ml carbenicillin and 25 μg/ml kanamycin, in Magenta boxes, at 25° C. for periods of 8 h low light/16 h dark. They were then removed from the Magenta boxes, potted up and transferred to the greenhouse.

Figure 9:
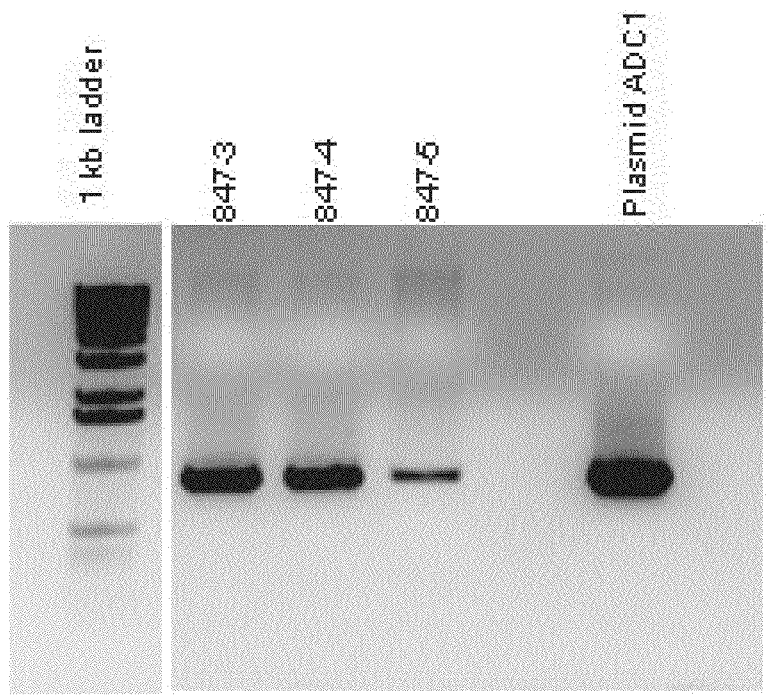
FIG. 9: PCR analysis of tomato genomic DNA prepared from wild-type and regenerated kanamycin-resistant shoots.

Integration of the *Arabidopsis* ADC1 gene into the tomato genome of $T_0$ plants was confirmed amplifying an 810 pb internal fragment by PCR, using the following pair of primers: ADC1-1F (5'-CCAGCTTCTGCATTTTCACA-3' SED ID NO: 15) and ADC1-1R (5'-CCATTGTTGTC-CATCTCGTG-3 SEQ ID NO: 16). Until now 3 independent transgenic lines have been obtained (FIG. 9).

TABLE 1

Composition of the different media

| MEDIUM | MSO | TRI1 | GCF10 | GCF11 | TRI2 |
| --- | --- | --- | --- | --- | --- |
| MS Salts | 4.3 g/L | 2.2 g/L | 4.3 g/L | 4.3 g/L | 2.2 g/L |
| Thiamine | 0.4 mg/L | 0.2 mg/L | 0.4 mg/L | 0.5 mg/L | 0.2 mg/L |
| Myo-Inositol | 100 mg/L | 50 mg/L | 100 mg/L | 100 mg/L | 50 mg/L |
| Glycine | — | — | — | 2.0 mg/L | — |
| Pyridoxine | — | — | 0.5 mg/L | 0.5 mg/L | — |
| Folic Acid* | — | — | — | 0.5 mg/L | — |
| Biotin* | — | — | — | 0.05 mg/L | — |
| Zeatin riboside* | — | — | 1.5 mg/L | 1.9 mg/L | — |
| NAA | — | — | — | — | 0.1 mg/L |
| IAA | — | 0.2 mg/L | 0.2 mg/L | — | — |
| Amcymidol* | — | — | — | — | 0.5 mg/L |
| Nicotinic Acid | — | — | 0.5 mg/L | 4.9 mg/L | — |
| Sucrose | 30 g/L | 15 g/L | 30 g/L | 30 g/L | 15 g/L |
| Carbenicillin* | — | — | 500 mg/L | 500 mg/L | 250 mg/L |
| Kanamycin* | — | — | 50 ± 10 mg/L | 50 ± 10 mg/L | 25 mg/L |
| Agar | — | 8 g/L | 8 g/L | 8 g/L | 8 g/L |
| pH | 5.8 | 5.9 | 5.9 | 5.9 | 5.9 |

*(Filter sterilised)

TABLE 2

AB (*Agrobacterium* medium)

| | |
| --- | --- |
| $K_2HPO_4$ | 3.0 g/L |
| $NaH_2PO_4$ | 1.0 g/L |
| $NH_4Cl$ | 1.0 g/L |
| $MgSO_4 \cdot 7H_2O$ | 0.3 g/L |
| KCl | 0.15 g/L |
| $CaCl_2$ | 0.01 g/L |
| $FeSO_4 \cdot 7H_2O$ | 2.5 g/L |
| Glucose | 5.0 g/L |
| Bacto-Agar | 15 g/L |

B. Characterization of Transgenic Plants

B.1. Estimation of ADC1 Expression Level by Real-Time RT-PCR

Total RNA was obtained from the aerial part of transformed and non-transformed *Licopersicum sculentum* plants as described in examples 1 and 2. The relative amount of ADC1 expression was determined by real-time RT-PCR as described in example 1 (section C.1). In this case 18S RNA was used as internal control to normalize the results.

Figure 10:
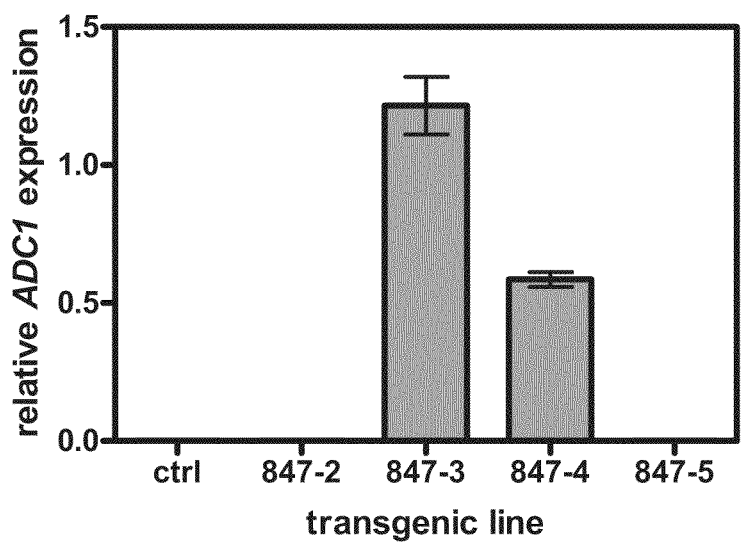
FIG. 10: Relative transcript levels of the *Arabidopsis* ADC1 gene in transgenic (847-2, 847-3, 847-4, 847-5) and control (ctrl) tomato plants.

High level of *Arabidopsis* ADC1 gene expression was detected in transgenic tomato lines 847-3 and 947-4, although the expression level varied to some extent (FIG. 10). No significant abnormal morphological and growth/development phenotypes were observed in the tomato plants overexpressing the *Arabidopsis* ADC1 gene.

---

The invention claimed is:

1. A method of producing a transgenic plant, the method comprising the steps of:
   transforming a cell of a plant with an exogenous arginine decarboxylase ADC1 gene sequence selected from the group consisting of:
   (a) a nucleotide sequence comprising sequence SEQ ID NO: 1, and
   (b) a nucleotide sequence coding for an amino acid sequence comprising sequence SEQ ID NO: 2,
   the nucleotide sequence being under the control of a promoter capable of functioning in the plant;
   regenerating a plant from said transformed cell; and
   selecting for a plant having the following differential traits when compared with a wild-type plant: (a) improved low-temperature stress resistance, (b) no developmental alterations, (c) no increased spermine level, and (d) an about 3.5-fold to an about 6-fold increased putrescine level.

2. The method according to claim 1, wherein the exogenous sequence comprises the sequence SEQ ID NO: 1.

3. The method according to claim 1, wherein the expression level of said exogenous arginine decarboxylase ADC1 gene is over-expressed in a transformant cell when compared with a cell not including the exogenous ADC1 gene.

4. A transformed plant obtained by the method as defined in claim 1.

5. A method of conferring low-temperature stress resistance to a plant comprising transforming the plant with an arginine decarboxylase ADC1 gene sequence selected from the group consisting of:
   (a) a nucleotide sequence comprising sequence SEQ ID NO: 1, and
   (b) a nucleotide sequence coding for an amino acid sequence comprising sequence SEQ ID NO: 2; and
   selecting for a plant having the following differential traits when compared with a wild-type plant: (a) improved low-temperature stress resistance, (b) no developmental alterations, (c) no increased spermine level, and (d) an about 3.5-fold to an about 6-fold increased putrescine level.

6. The method according to claim 5, wherein the exogenous sequence comprises the sequence SEQ ID NO: 1.

7. The method according to claim 2, wherein the expression level of said exogenous arginine decarboxylase ADC1 gene is over-expressed in transformant cells when compared with cells not including the exogenous ADC1 gene.

8. The method according to claim 5, wherein the expression level of said exogenous arginine decarboxylase ADC1 gene is over-expressed in a transformant cell when compared with a cell not including the exogenous ADC1 gene.

9. The method according to claim 6, wherein the expression level of said exogenous arginine decarboxylase ADC1 gene is over-expressed in a transformant cell when compared with a cell not including the exogenous ADC1 gene.

10. The method according to claim 3, wherein the putrescine level is increased in the transformant cell.

11. The method according to claim 2, wherein the putrescine level is increased in the transformant cell.

12. The method according to claim 7, wherein the putrescine level is increased in the transformant cell.

13. The method according to claim 8, wherein the putrescine level is increased in the transformant cell.

14. The method according to claim 9, wherein the putrescine level is increased in the transformant cell.

15. The method according to claim 1, wherein the exogenous sequence consists of the sequence SEQ ID NO: 1.

16. The method according to claim 5, wherein the exogenous sequence consists of the sequence SEQ ID NO: 1.

* * * * *